United States Patent
Yamada

(10) Patent No.: US 7,792,340 B2
(45) Date of Patent: Sep. 7, 2010

(54) INFORMATION PROCESSING APPARATUS AND METHOD

(75) Inventor: Naoki Yamada, Soka (JP)

(73) Assignee: Canon Kabushiki Kaisha, Tokyo (JP)

(*) Notice: Subject to any disclaimer, the term of this patent is extended or adjusted under 35 U.S.C. 154(b) by 902 days.

(21) Appl. No.: 11/625,173

(22) Filed: Jan. 19, 2007

(65) Prior Publication Data

US 2007/0177783 A1 Aug. 2, 2007

(30) Foreign Application Priority Data

Jan. 27, 2006 (JP) .............................. 2006-019768

(51) Int. Cl.
*G06K 9/00* (2006.01)
(52) U.S. Cl. ..................... 382/128; 382/286
(58) Field of Classification Search ........................ None
See application file for complete search history.

(56) References Cited

U.S. PATENT DOCUMENTS

| | | | |
|---|---|---|---|
| 6,692,448 B2 | 2/2004 | Tanaka et al. | |
| 7,039,225 B2 | 5/2006 | Tanaka et al. | |
| 2002/0161446 A1* | 10/2002 | Bryan et al. | 623/17.15 |
| 2005/0189501 A1* | 9/2005 | Sato et al. | 250/492.22 |
| 2006/0242159 A1* | 10/2006 | Bishop et al. | 707/10 |
| 2007/0112433 A1* | 5/2007 | Frederick et al. | 623/22.41 |

FOREIGN PATENT DOCUMENTS

JP 2002-085434 A 3/2002

* cited by examiner

*Primary Examiner*—Charles Kim
(74) *Attorney, Agent, or Firm*—Canon U.S.A., Inc., IP Division

(57) ABSTRACT

An apparatus and method for displaying, on a medical image, template data corresponding to an implant. The apparatus and method include a storing the template data and a predetermined portion distance of a predetermined portion of a representation by the template data, a displaying the stored template data, measuring length information of the displayed template data, specifying an error range of the variable magnification of the displayed template data, and judging, based on the measured length information and the stored predetermined portion distance, whether the variable magnification of the displayed template data is within the specified error range.

8 Claims, 14 Drawing Sheets

RELATED ART

INFORMATION PROCESSING APPARATUS AND METHOD

BACKGROUND OF THE INVENTION

1. Field of the Invention

The present invention relates to information processing apparatuses and methods therefor. Specifically, the present invention relates to processing of template data for use in determining (designing) the size of an implant (artificial bone) before embedding the implant into a human body, and in particular, to template data processing in the field of orthopedics.

2. Description of the Related Art

In the case of bone resection in surgery in medical fields such as orthopedics, implants, e.g., artificial bones, are used. In many instances, standard sized/shaped implants cannot be used and specially designed implants tailored to a particular patient's physique are required. Typically, a standard model is prepared, from which the implant for a particular patient is re-shaped.

When the standard model is selected, the following operations (1) and (2) are typically performed:

(1) An X-ray image formed by X-ray imaging is output onto a film; and (2) The obtained film is superposed onto a transparent template sheet modeling an edge shape of a standard model. The transparent template sheet is then visually confirmed concerning the degree of conformity in shape between the standard model and the affected area.

These operations allow determination of the size of an implant that can fit the affected area.

In recent years, with widespread use of digital X-ray imaging apparatuses, a diagnosis can be made by inputting X-ray images formed by an X-ray imaging apparatus into a terminal device, such as a personal computer, and displaying the input digital images on a high definition monitor. In this environment, determination of an implant size is done using the following operations (1) and (2):

(1) A template sheet is captured as digital information (template data) by using an image scanning apparatus such as a scanner; and (2) The captured template data is displayed on an X-ray digital image in overlay form on a monitor, and the displayed template data is used to determine an implant size. Japanese Patent Laid-Open No. 2002-85434 discloses a method for selecting a standard model by using a digital X-ray imaging apparatus.

However, regarding an X-ray image formed by the X-ray imaging apparatus, in general, an actually formed X-ray image is approximately 10% larger in size than an object because, in image formation, a distance between an X-ray tube and a sensor differs from a distance between the X-ray tube and a patient. There are many template sheets created in which the enlargement factor is considered. When an image scanning apparatus, such as a scanner, scans a template sheet, or in processing after the image scanning apparatus scans a template sheet, the scanning resolution may change. Thus, it is not guaranteed that the X-ray image and the template data are equal in enlargement factor.

An example of a template sheet is illustrated in FIG. 1. A template sheet 11 includes plural types of standard model data items 12 indicating the sizes and shapes of implants, size representations 13 representing the sizes of the standard model data items, a value representation 14 representing an enlargement factor of the template sheet 11, and a scale 15 for measuring the enlargement factor.

The template sheet 11 is created considering a magnification of 10%. Thus, the scale 15 has an actual length of 11 centimeters when the scale 15 is actually measured with a ruler. When the template sheet 11 is digitized by an image scanning apparatus, such as a scanner, the resolution of the digitized template data may change in the middle of digitization. A change in resolution changes a preset enlargement factor and an enlargement factor of an image actually displayed on a monitor. Determination of an implant size by using template data having a changed enlargement factor leads to determination of a wrong implant size, thus resulting in a decrease in diagnosis efficiency of a doctor. Therefore, it is very important to maintain accuracy of an enlargement factor of template data.

SUMMARY OF THE INVENTION

According to an aspect of the present invention, an information processing apparatus for displaying, on a medical image, template data corresponding to an implant, includes a storage unit configured to store the template data and a predetermined portion distance of a predetermined portion of a representation by the template data, a display unit configured to display the template data stored in the storage unit, a measurement unit configured to measure length information of the template data displayed on the display unit, a specification unit configured to specify an error range of variable magnification of the template data displayed on the display unit, and a judgment unit configured to determine, based on the length information measured by the measurement unit and the predetermined portion distance stored by the storage unit, whether the variable magnification of the template data displayed on the display unit is within the error range specified by the specification unit.

Further features of the present invention will become apparent from the following description of exemplary embodiments with reference to the attached drawings.

The accompanying drawings, which are incorporated in and constitute a part of the specification, illustrate exemplary embodiments of the invention and, together with the description, serve to explain the principles of the invention.

DESCRIPTION OF THE EMBODIMENTS

Exemplary embodiments of the present invention will now be described in detail in accordance with the accompanying drawings.

First Exemplary Embodiment

Figure 1:
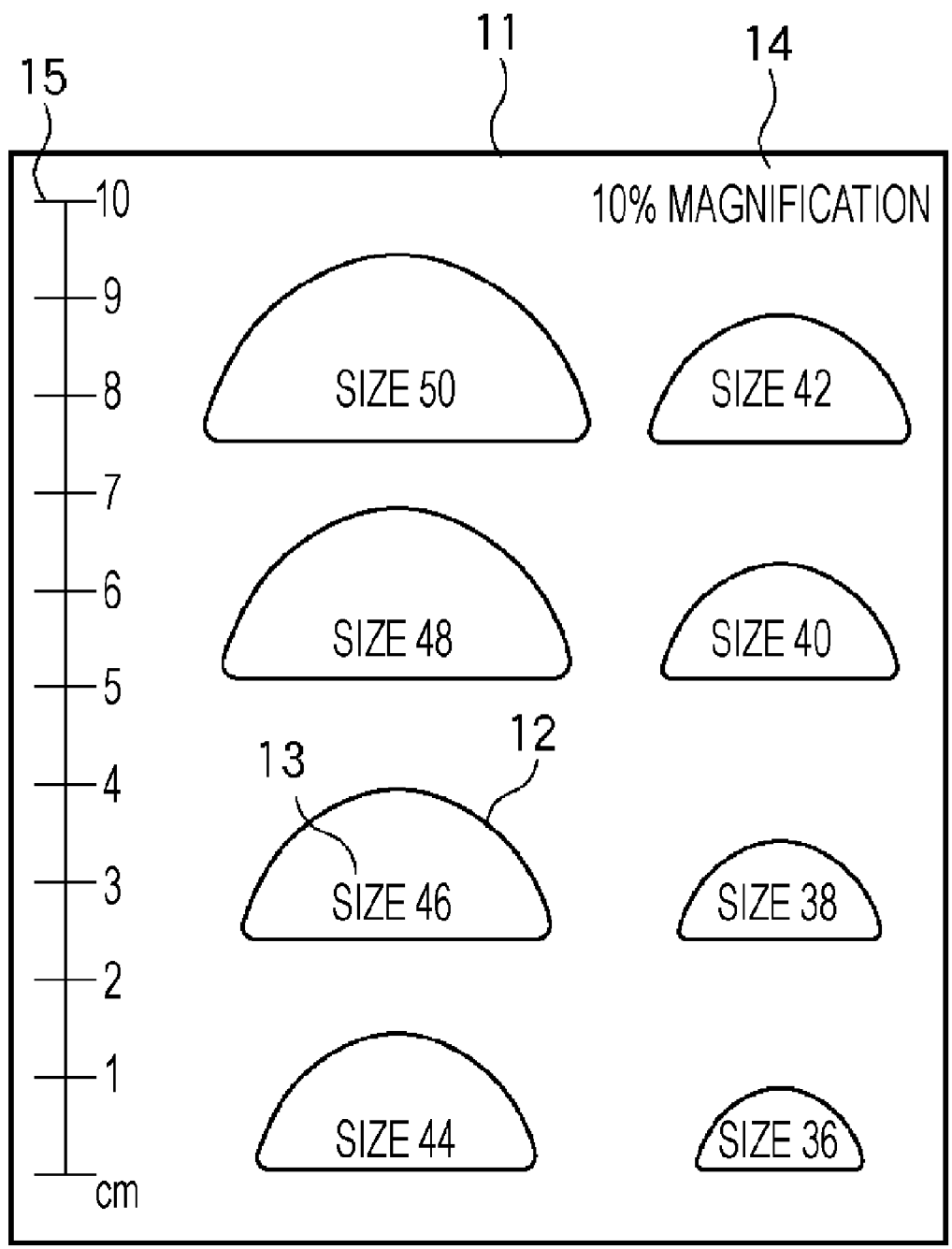
FIG. 1 is an illustration of an example of a template.
Figure 2:
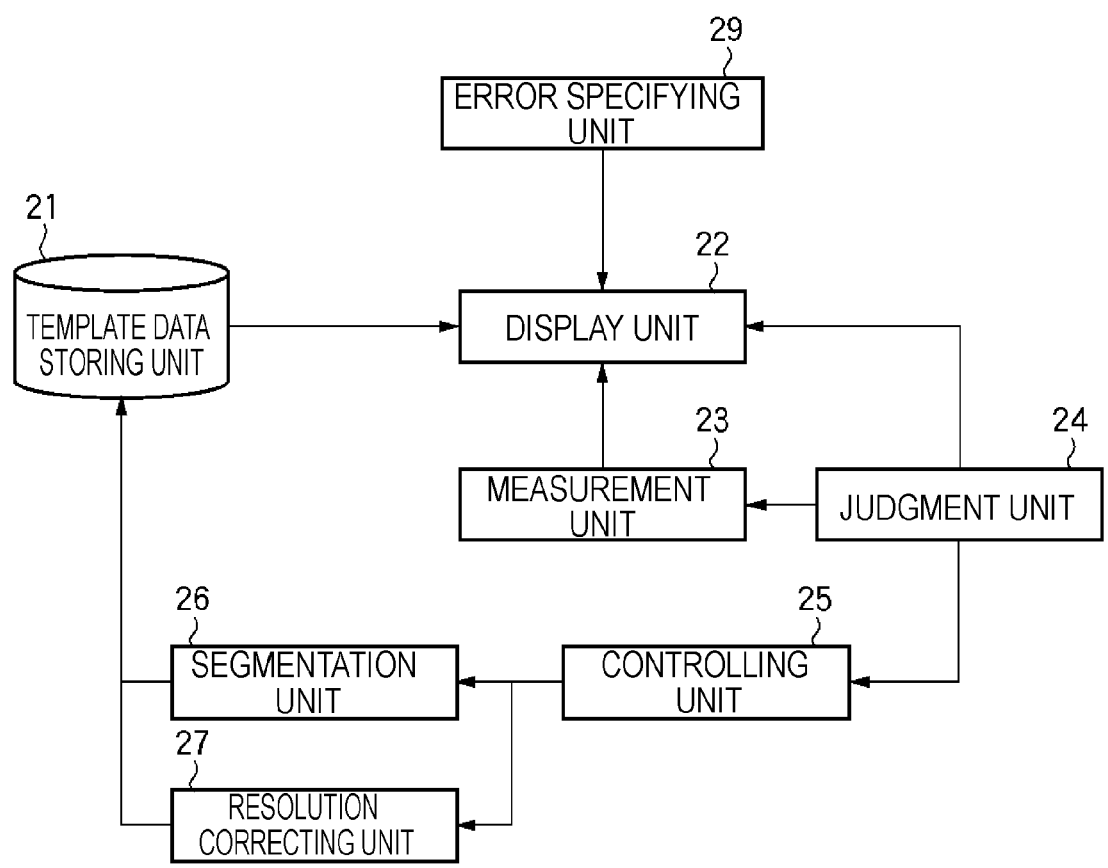
FIG. 2 is a block diagram illustrating a functional configuration of a template data processing device according to a first exemplary embodiment of the present invention.

FIG. 2 illustrates the configuration of functions of a template data processing device according to a first exemplary embodiment of the present invention. The functions are realized by standard elements provided in an information processing apparatus such as a personal computer. The elements include, for example, a CPU (central processing unit), a RAM (random access memory), a ROM (read-only memory), a hard disk, an external storage device, a network interface, a display, a keyboard, and a mouse.

Referring to FIG. 2, a template data storing unit 21 stores digitized template data, a distance of a predetermined portion of the template data, and extended-distance data based on considering an enlargement factor. The digitized template data represents data obtained by using an image scanning apparatus, such as a scanner, to scan a template sheet, and template data created as digital data by using software running on a computer. The template data storing unit 21 is for example, an external storage device.

The template data storing unit 21 also stores template data representing an arrangement of a plurality of standard models, and template data representing an arrangement of standard models that are segmented from template data representing an arrangement of a plurality of standard models. The template data stored in the template data storing unit 21 can be displayed on a display unit 22. The display unit 22 is formed by a common display apparatus such as a CRT (cathode-ray tube) display or a liquid crystal display.

By operating an instruction input device (not shown) for the template data displayed on the display unit 22, measurement and input of an enlargement factor and template data segmentation can be executed. The instruction input device is formed by a common input device such a mouse or keyboard.

A measurement unit 23 measures template-length information, such as the scale 15 of template data, for determining an enlargement factor of the template data, as well the length of the template data itself. A value measured by the measurement unit 23 is displayed on the display unit 22. Based on the measured information, a judgment unit 24 judges whether an enlargement factor of template data lies within an error range specified by an error specifying unit 29.

The judgment of the enlargement factor may be visually performed by a person. By inputting the length of the scale 15 or a template sheet itself beforehand, or an enlargement factor of a template sheet into the instruction input device, the judgment of the enlargement factor may be performed based on the input value.

In addition, the judgment of the enlargement factor may be performed by comparing the distance of the predetermined portion of the template sheet that is stored in the template data storing unit 21, and extended-distance data calculated based on the enlargement factor of the template sheet. Furthermore, in the judgment, if the enlargement factor of the template data is within the error range specified by the error specifying unit 29, the judgment unit 24 judges that the enlargement factor is accurate. If the enlargement factor is outside the error range, the judgment unit 24 judges that the enlargement factor is not accurate.

If the judgment unit 24 has judged that the enlargement factor is within the error range specified by the error specifying unit 29, a controlling unit 25 allows a segmentation unit 26 to perform template data segmentation. If the judgment unit 24 has judged that the enlargement factor is not within the error range specified by the error specifying unit 29, the controlling unit 25 prohibits the segmentation unit 26 from performing template data segmentation, and outputs a template-data-resolution correcting instruction to a resolution correcting unit 27.

The resolution correcting unit 27 corrects the resolution of the template data to match the resolution of an image formed by X-ray imaging. If the judgment unit 24 has judged that the enlargement factor of the template data is not within the error range specified by the error specifying unit 29, the resolution correcting unit 27 is controlled to correct the resolution of the template data. The corrected template data is measured again by the measurement unit 23, and the judgment unit 24 judges whether the enlargement factor of the corrected template data is within the error range specified by the error specifying unit 29.

If the judgment unit 24 has judged that the enlargement factor of the corrected template data is within the error range, the corrected template data is again stored in the template data storing unit 21. In addition, each template data item segmented by the segmentation unit 26 is also stored in the template data storing unit 21. The measurement unit 23, the judgment unit 24, the controlling unit 25, the segmentation unit 26, and the resolution correcting unit 27 can be realized by, for example, a program executed under the control of a CPU in an information processing apparatus. Alternatively, hardware dedicated for realizing each function may be provided. Finally, by allowing hardware and software to operate cooperatively, the functions can also be realized.

Figure 3:
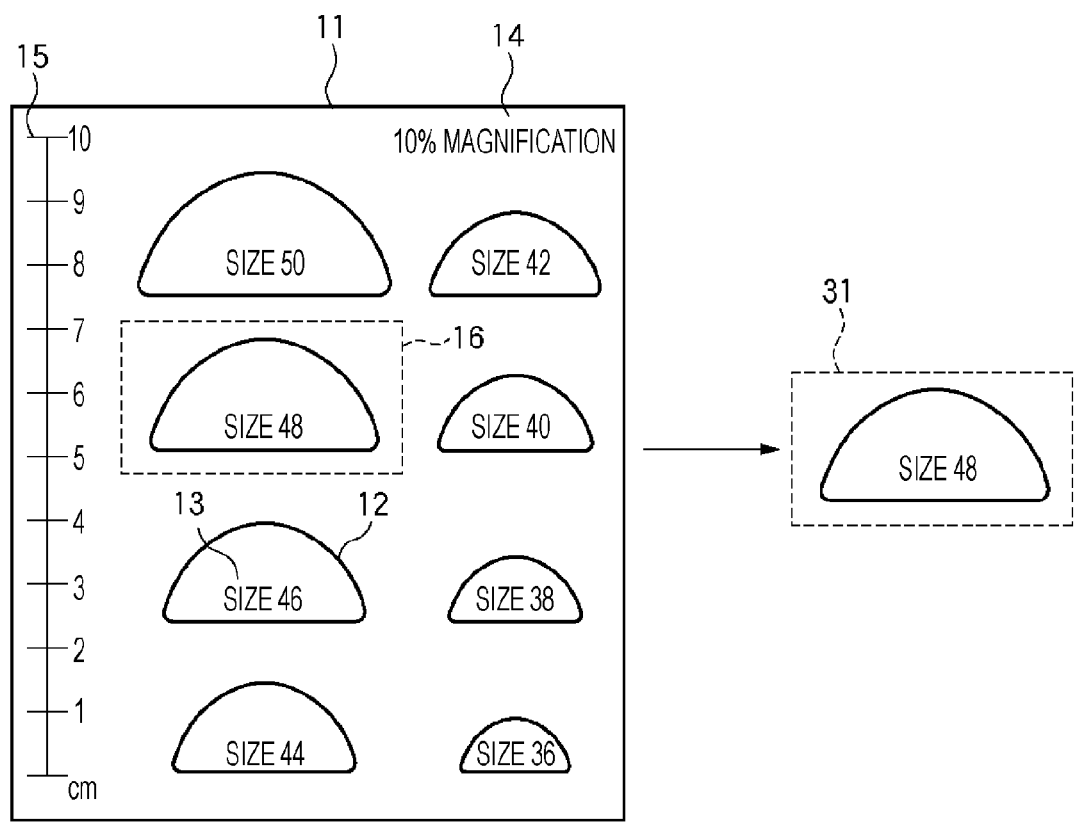
FIG. 3 is an illustration of an example of template segmentation in the first embodiment.

An example of template data segmentation by the segmentation unit 26 is described below with reference to FIG. 3. FIG. 3 illustrates an example of template data segmentation by the segmentation unit 26 in the present embodiment.

By operating the instruction input device, i.e., a mouse, the user specifies a segmentation range 16 (the dotted line portion illustrated in FIG. 3) of standard model data on the template sheet 11 displayed on the display unit 22. The template data processing device performs processing to generate a standard model data item 31 that is specified and segmented from the template sheet 11.

Each specified and segmented standard model data item is stored as a template data item in the template data storing unit 21. By reading the template data item from the template data storing unit 21, the read template data item is displayed on an X-ray image in overlay form. Displaying the template data item in overlay form makes it possible to easily determine the size of an implant for use.

Figure 4:
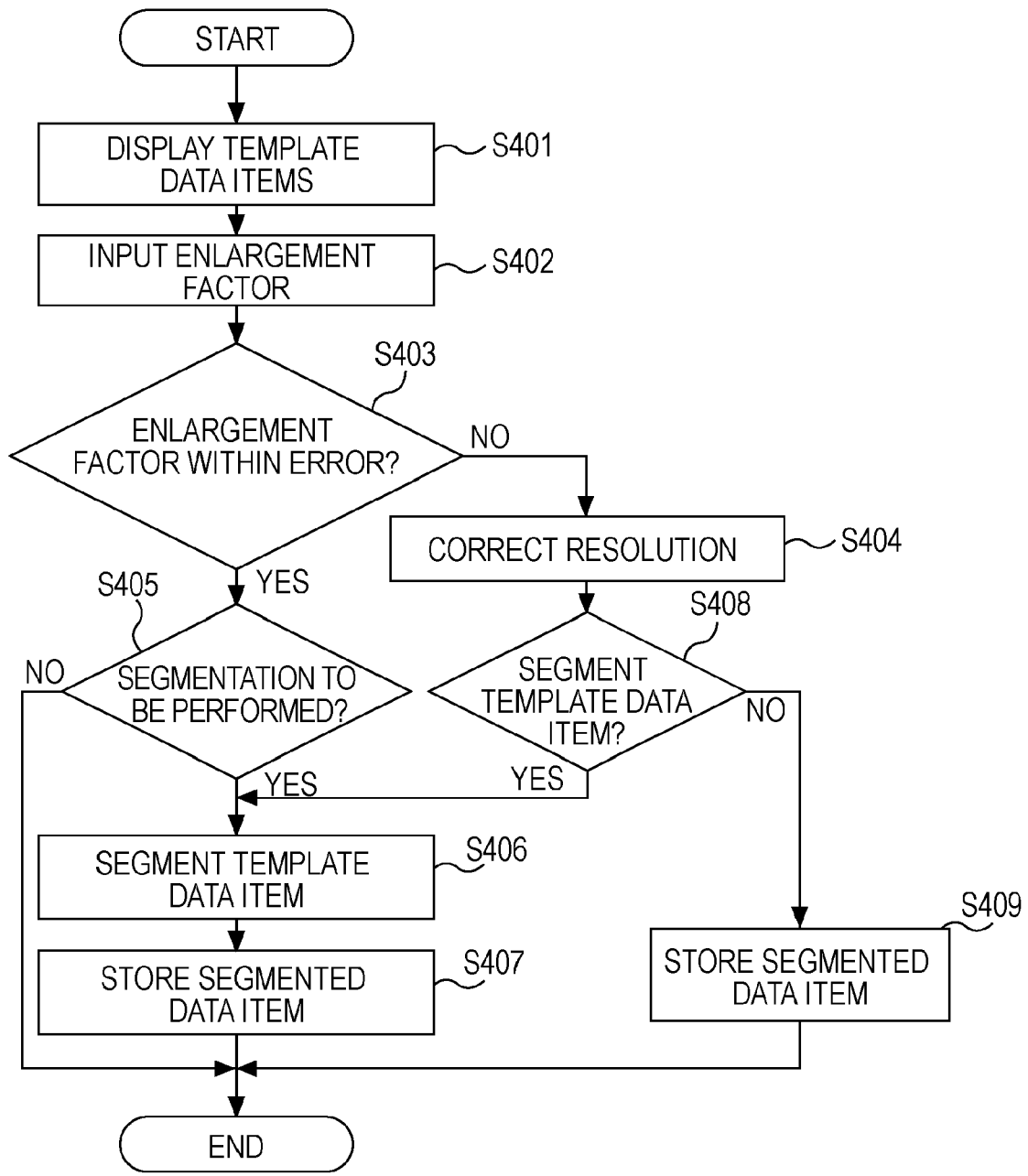
FIG. 4 is a flowchart illustrating a process executed by the template data processing device according to the first embodiment.

Next, a process executed by the template data processing device is described with reference to FIG. 4. FIG. 4 is a flowchart illustrating the process executed by the template data processing device according to the present embodiment.

In step S401, the template data items stored in the template data storing unit 21 are displayed on the display unit 22. Next, after receiving a user's operation instruction via the instruction input device, the template data processing device segments each template data item. In the first embodiment, it is confirmed whether an enlargement factor of the template data items displayed on the display unit 22 is within the error range specified by the error specifying unit 29. Accordingly, in order to judge the enlargement factor of the displayed template data items, in step S402, an enlargement factor is input.

There are several methods by which the enlargement factor can be input. In one method, the measurement unit 23 is used to measure the scale 15 or the length of each template data item displayed on the display unit 22, and the enlargement factor is input based on the measured value. In another method, the distance of a predetermined portion of a template represented by a template data item stored in the template data storing unit 21, and extended-distance data calculated on the basis of the enlargement factor of the stored template data item are read, and an enlargement factor based on the read extended-distance data is input.

In step S403, the judgment unit 24 determines whether the input enlargement factor is within the error range specified by the error specifying unit 29. f it is determined that the input enlargement factor is not within the error range ("NO" in step S403), the process proceeds to S404, and the resolution of the template data item is corrected by the resolution correcting unit 27.

Next, in step S408, it is determined whether a template data item is to be segmented. If the template data item is to be segmented ("YES" in step S408), the process proceeds to step S406. If the template data item is not to be segmented ("NO" in step S408), the process proceeds to step S409, and the template data item having the resolution corrected is stored in the template data storing unit 21 again.

One method of determining whether the template data item is to be segmented is performed by monitoring, for example, an instruction operation on the instruction input device. For example, in a case where the template sheet 11 is displayed on the display unit 22, and an instruction operation is performed within a predetermined time, it is determined that the template data item is to be segmented ("YES" in step S408). In a case in which no instruction operation is performed when the predetermined time passes, it is determined that the template data item is not to be segmented ("NO" in step S408).

In addition, when the resolution is corrected, measurement is performed again by the measurement unit 23. When the judgment unit 24 judges based on the measured value that the input enlargement factor is within the specified error range, the template data item having the resolution corrected is stored in the template data storing unit 21 for updating.

If the input enlargement factor lies within the error range ("YES" in step S403), the process proceeds to step S405. In step S405, it is determined whether the template data item is to be segmented. If the template data item is to be segmented ("YES" in step S405), the process proceeds to step S406. If the template data item is not to be segmented ("NO" in step S405), the process finishes.

In step S406, a standard model data item is segmented from the template sheet 11. The enlargement factor of the template sheet 11 is already within the error range specified by the error specifying unit 29. Thus, each standard model data item can be segmented. Accordingly, by operating the instruction input device to specify a segmentation range, the segmentation range is segmented by the segmentation unit 26.

In step S407, the standard model data item segmented as each template is stored as a template data item in the template data storing unit 21. By reading the stored template data items from the template data storing unit 21, and displaying the read template data items (standard model data items) on an X-ray image in overlay form, the size of an implant to be actually used can be determined.

Next, the method of measurement for judging the enlargement factor on the basis of the measured value from the measurement unit 23 is described below.

Figure 5:
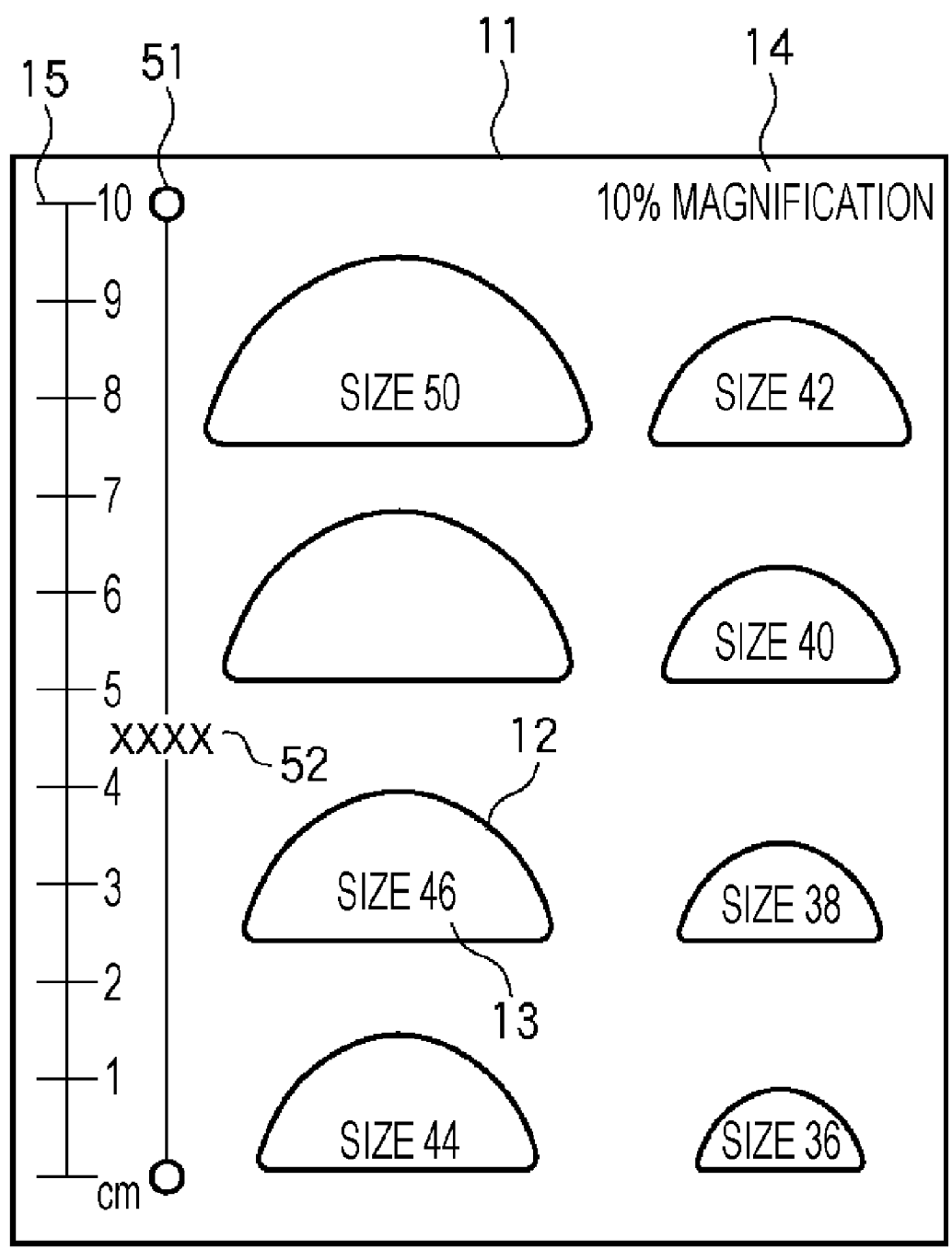
FIG. 5 is an illustration of a measurement method for use in determining an enlargement factor by a measurement unit in the first embodiment.

FIG. 5 illustrates a measurement method for judging the enlargement factor by using the measurement unit 23 in the present embodiment. By operating the instruction input device, the user can measure the length of the scale 15. FIG. 5 illustrates a measurement line 51 for the scale 15, and a measured value 52 on the measurement line 51. By viewing the measurement value 52, the user can judge whether the enlargement factor of a template data item is within the error range specified by the error specifying unit 29.

Before measurement by the measurement unit 23, the instruction input device is used to input the length of the scale 15 on an actual template sheet, and one or both of a distance of a predetermined portion of the template and an enlargement factor of the predetermined portion. Alternatively, the distance of the predetermined portion of the template represented by the template data item and extended-distance data calculated based on the enlargement factor of the predetermined portion are read from the template data storing unit 21. By using these data items, based on the measurement value 52, the judgment unit 24 can judge, without an instruction by the user, whether the enlargement factor of the template data item is within the error range specified by the error specifying unit 29.

As described above, according to the present embodiment, a template data item that matches the enlargement factor of an X-ray image can be created. This can prevent selection of a standard model having a wrong size when the size of an implant is determined.

Second Exemplary Embodiment

Figure 6:
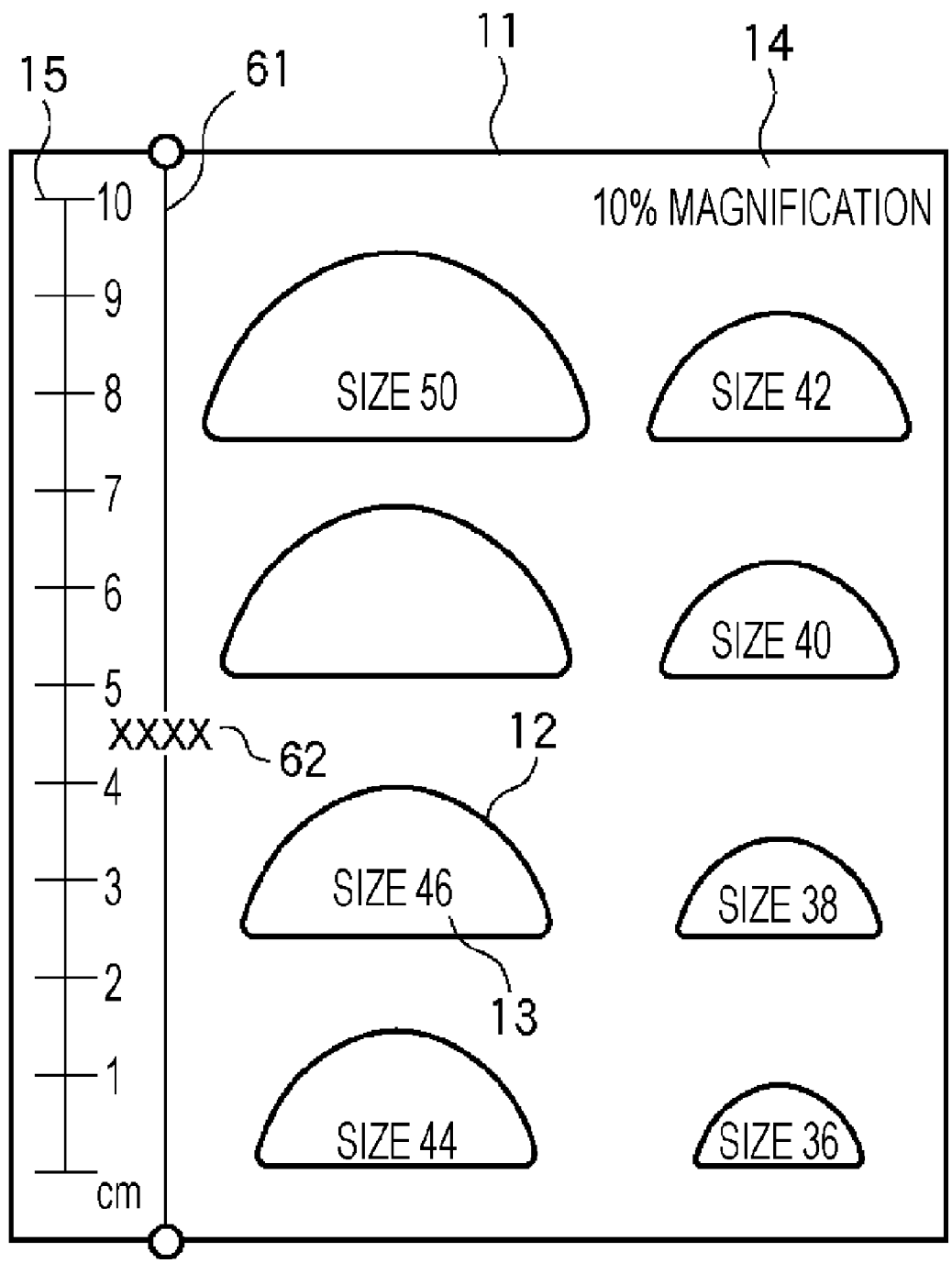
FIG. 6 is an illustration of an example of measuring the length of a template in a second exemplary embodiment of the present invention.

In a second exemplary embodiment of the present invention, a method for measuring the length of a representation by template data by the measurement unit 23, different from that in the first embodiment, is described. FIG. 6 illustrates an example, according to the present embodiment, of measuring, by the measuring unit 23, the length of a representation by template data itself.

By operating the instruction input device, the user can measure the length of the template sheet 11 itself. FIG. 6 illustrates a measurement line 61 representing the length of the template sheet 11 itself and a measured value 62 representing the length of the template sheet 11. By viewing the measured value 62, the user can judge whether the enlargement factor of the template sheet 11 is within the error range specified by the error specifying unit 29.

In addition, before measurement by the measurement unit 23, the instruction input device is used to input the length of an actual template itself, and one or both of a distance of a predetermined portion of the template and an enlargement factor of the predetermined portion. Alternatively, the distance of a predetermined portion of the template and extended-distance data, calculated based on the enlargement factor of the predetermined portion, are read from the template data storing unit 21.

By using these data items, based the measured value 62, the judgment unit 24 can judge, without an instruction by the user, whether the enlargement factor of the template data item is within the error range specified by the error specifying unit 29.

In the first and second embodiments, a configuration in which the measurement unit 23 is used to judge the enlargement factor of a template data item has been described. However, the present invention is not limited to the described configuration. For example, enlargement factor judgment can be performed on the basis of the result of detecting the length of the scale 15 on the template sheet 11 or the template sheet 11 itself by using an image processing technology such as object recognition.

Third Exemplary Embodiment

Next, a method for reducing the working load of a user is described.

In order to determine the size of an implant for use in surgery, the user displays digitized standard model data items on an X-ray image in overlay form by using the display unit 22, and finds a standard model data item of a standard model that fits an affected area in size. When the user finds an implant size that fits the affected area, the user needs to find the implant size while switching standard model data items having different sizes. In addition, in order to find the standard model data item that fits the affected area, the user must frequently turn each standard model data item and must move the standard model data item.

Examples of operations of the related art are illustrated in FIGS. 7A to 7D. FIGS. 7A to 7D illustrate a screen W101 which displays a standard model data item on an X-ray image in overlay form and which is used for finding an affected area size. The screen W101 includes a screen portion W102 for selecting a standard model data item that is a template data item to be displayed in overlay form, and a screen portion W103 for use in an actual operation.

Figure 7A:
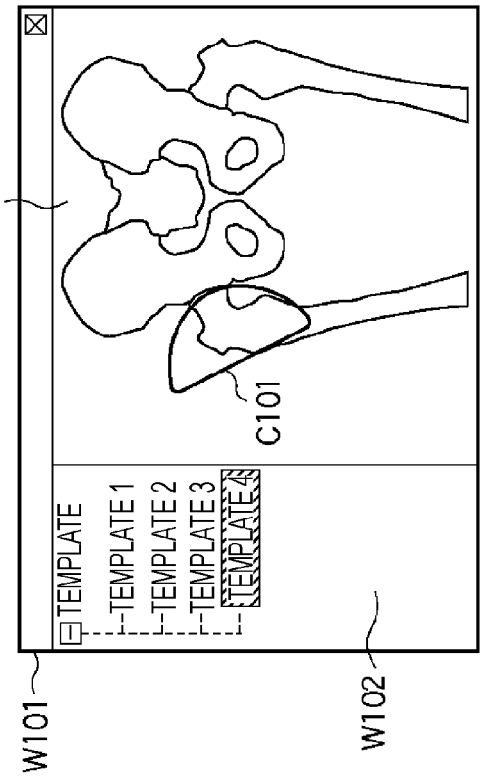
FIGS. 7A, 7B, 7C, and 7D are illustrations of examples of operations of the related art.

When the user determines an implant size, as shown in FIG. 7A, the user selects a standard model data item having a preset size on the screen portion W102. In FIG. 7A, template 4 is selected. Selection of a template data item on the screen portion W102 displays the selected template data item on the X-ray image in overlay form. In FIG. 7A, template data item C101 is displayed.

Figure 7B:
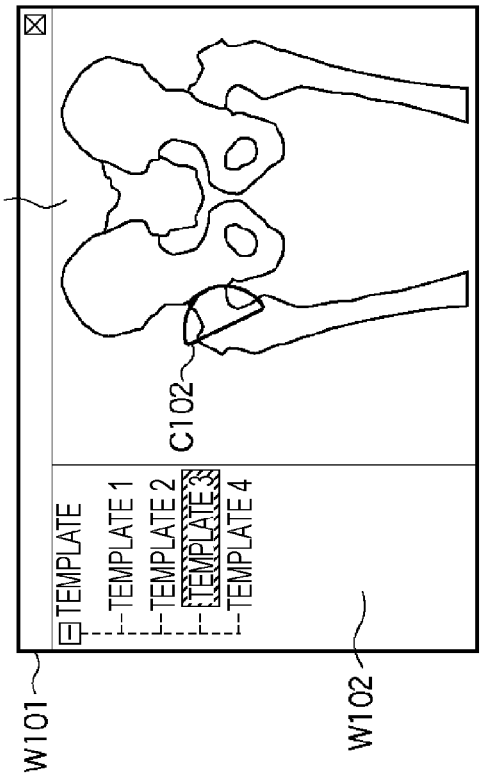

Next, as illustrated in FIG. 7B, in order to measure the size of an affected area, the user turns and moves the template data item C101 displayed in overlay form in the vicinity of the affected area. The user attempts to, for example, measure the size. Since the template data item C101 does not fit the shape of the affected area, it is presumed to be larger than the affected area.

Figure 7C:
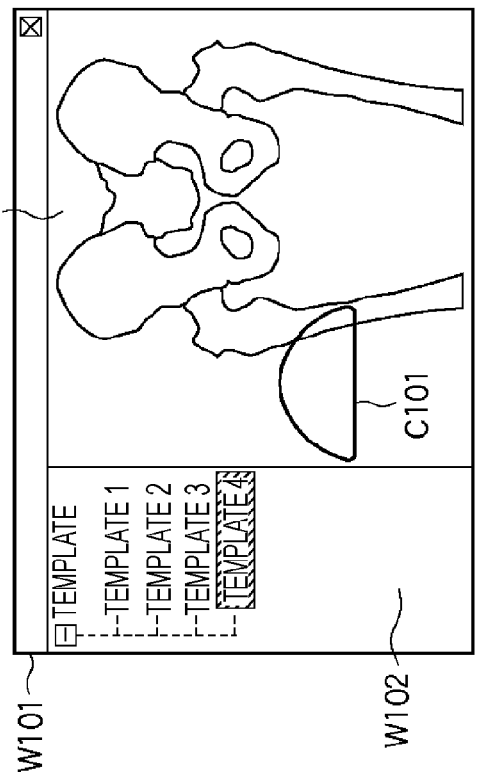
Figure 7D:
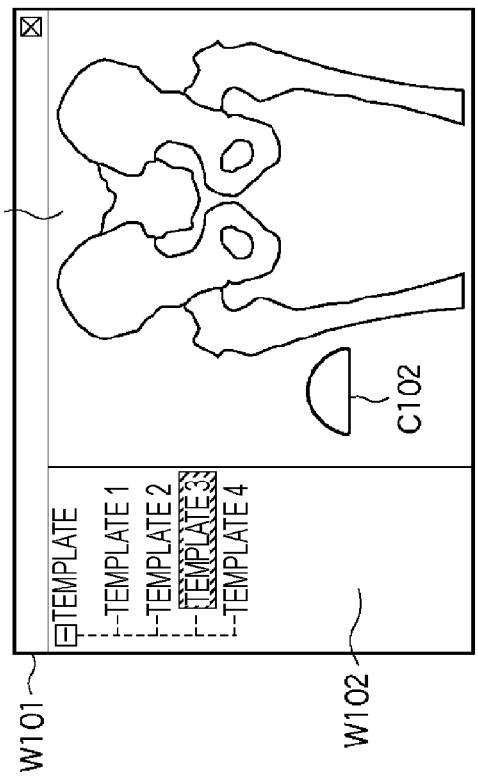

When the template data item C101 is too large, as illustrated in FIG. 7B, the user, via screen W101, selects another template data item, which is smaller in size than the template data item C101. In FIG. 7*c*, template 3 is selected. Re-selection of a template data item on the screen portion W102 displays the selected template data item on the X-ray image in overlay form. In FIG. 7C, a template data item C102 is displayed. As illustrated in FIG. 7D, the user attempts to measure the size by turning and moving the template data item C102 displayed in overlay form in the vicinity of the affected area.

The above described operations allow the user to determine the size of an implant for use in surgery by using template data items. However, in these operations, whenever the user selects a template data item, the user must turn and move the template data item. Thus, the user is required to perform cumbersome and complicated work, thereby reducing the user's work efficiency.

Accordingly, in a third exemplary embodiment of the present invention, a template data processing device for improving working efficiency in view of the above described problem is described below.

Figure 8:
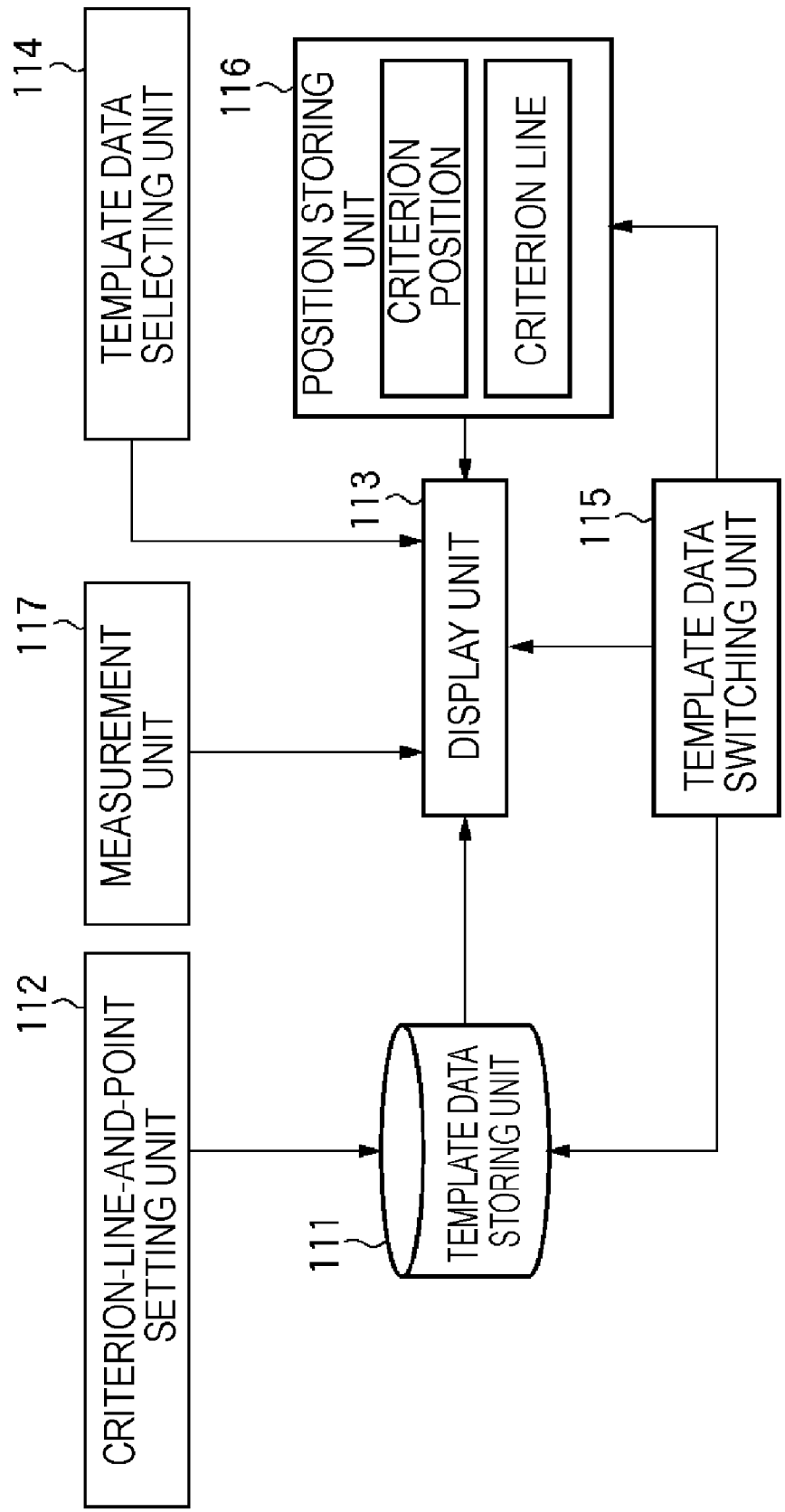
FIG. 8 is a block diagram illustrating a functional configuration of a template data processing device according to a third exemplary embodiment of the present invention.

FIG. 8 is a block diagram illustrating a functional configuration of the template data processing device according to the present embodiment. This functional configuration is realized by standard elements provided in a multipurpose computer, such as a personal computer, that is an information processing apparatus. The elements include, for example, a CPU, a RAM, a ROM, a hard disk, an external storage device, a network interface, a display, a keyboard, and a mouse.

Referring to FIG. 8, a template data storing unit 111 stores digitized original template data items, and template data items (standard model data items) segmented from the original template data items. The digitized template data items represent template data items created as digital data items by scanning template sheets of the related art by using an image scanning apparatus such as a scanner. The template data storing unit 111 is formed by, for example, an external storage device.

For each template data item stored in the template data storing unit 111, a criterion line and a criterion point can be set. The criterion line and point are set such that the user operates the instruction input device. This is executed by a criterion-line-and-point setting unit 112.

By using the criterion-line-and-point setting unit 112, the criterion and point can be set for the standard model data item. The criterion and point are used when the template data item is actually displayed on an X-ray image in overlay form. The existence of the criterion and point enables the user to easily switch, based on the criterion and point, a standard model data item displayed in overlay form.

Figure 9A:
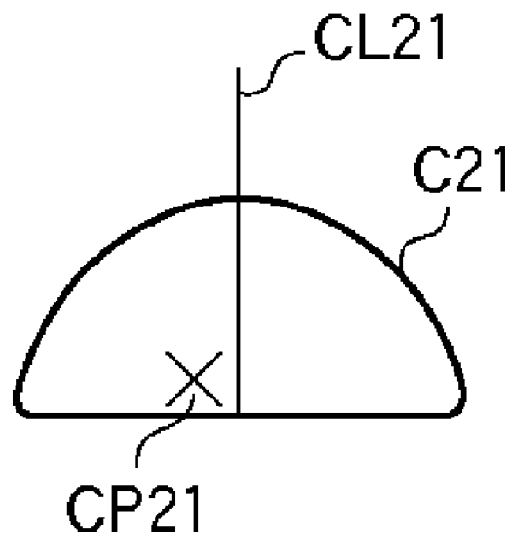
FIGS. 9A and 9B are illustrations of an example of setting criterion line and point for standard model data.
Figure 9B:
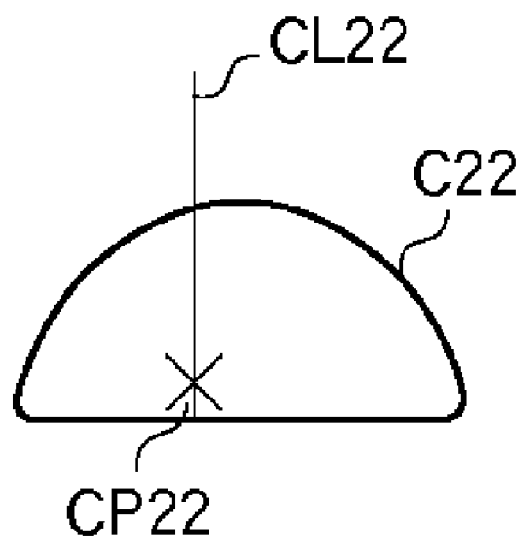

FIGS. 9A and 9B are illustrations of examples of setting a criterion line and a criterion point for a standard model data item in the present embodiment. FIGS. 9A and 9B illustrate segmented template data items C21 and C22, respectively. In the example illustrated in FIG. 9A, by operating the instruction input device, the user can set a criterion line CL21 and a criterion point CP21 for a template data item C21. In addition, as illustrated in FIG. 9B, the user can set a criterion line CL22 and a criterion point CP22. In the example illustrated in FIG. 9B, the criterion line CL22 is set so as to pass on the criterion point CP22. In other words, the user can set a criterion line and a criterion point at any position in the template data item.

That is, as illustrated in FIG. 9A, the criterion line CL21 and the criterion point CP21 are at different positions, respectively. Alternatively, as illustrated in FIG. 9B, the criterion line CL22 and the criterion point CP22 may intersect.

The template data item for which the criterion line and point set by the criterion-line-and-point setting unit 112 is stored in the template data storing unit 111 again. The template data item stored in the template data storing unit 111 is displayed on the screen W101 for displaying a template data item on an X-ray image for implant size determination by a display unit 113. The display unit 113 is realized by a common display device such as a CRT display or a liquid crystal display.

By operating the instruction input device, the user can select and switch a template data item on the screen W101 displayed by the display unit 113. In order to switch template data items to be displayed on the screen portion W102, the user can select an arbitrary template data item by using a template data selecting unit 114. This allows a template data switching unit 115 to switch the template data item displayed on the screen portion W103.

Position information of the criterion line and point of a template data item displayed before template-data-item switching are temporarily stored in a position storing unit 116. The template data switching unit 115 displays a switched template data item on the screen portion W103 while referring to positions of the criterion line and point which are stored in the position storing unit 116. This allows the user to display a template data item at a targeted position after performing template-data-item switching without performing operations such as turning and moving.

In the present embodiment, a coordinate system defining the position of a template data item, and the positions of criterion line and criterion point of the template data item is represented by, for example, an X-Y coordinate system having a top left corner of an image display region (e.g., the screen portion W103) as an origin, a horizontal direction as an X axis, and a vertical direction as a Y axis. In addition, regarding angle information of the criterion line, for example, when a line segment in parallel with the X axis from an end point of the criterion line is defined, an angle between the line segment and the criterion line is used as the angle of the criterion line. These definitions are examples, and any coordinate system that would enable practice of the present invention is applicable.

Fourth Exemplary Embodiment

Figure 10A:
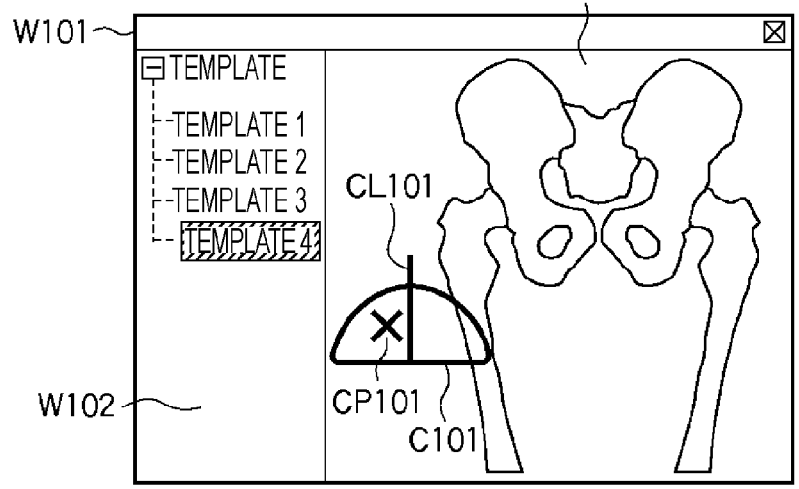
FIGS. 10A, 10B, and 10C are illustrations of examples of template data items displayed in the third embodiment.
Figure 10B:
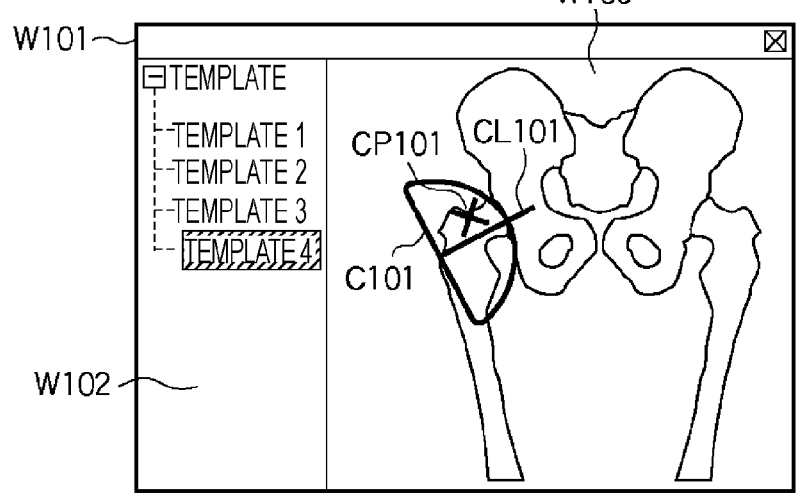
Figure 10C:
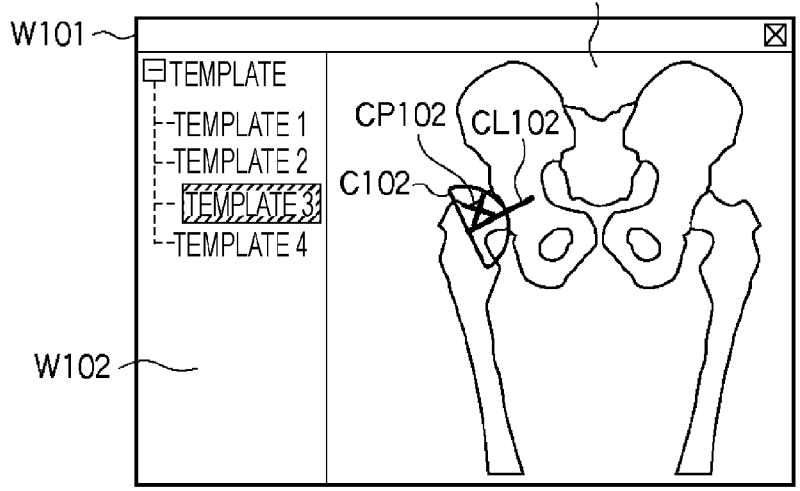

A template display method by the template data switching unit 115 is described below. FIGS. 10A, 10B, and 10C illustrate display examples of template data items in a fourth exemplary embodiment of the present invention.

The display unit 113 displays the screen W101 for use in displaying the template data item on the X-ray image in overlay form for determining an implant size. In order to determine the implant size, the user selects a template data item on the screen portion W102 by operating the instruction input device. In FIG. 10A, template 4 is selected.

When the template data item is selected on the screen portion W102, the selected template data item is read from the template data storing unit 111 and is displayed on the screen portion W103. In FIG. 10A, a template data item C101 is displayed.

The template data item C101 has a criterion line CL101 and criterion point CP101 already set by the criterion-line-and-point setting unit 112. Simultaneously with displaying of the template data item C101, the criterion line CL101 and the criterion point CP101 may be displayed on the screen portion W103 or may be hidden.

After the template data item C101 is displayed, the user selects the template data item C101 by operating the instruction input device, and, as illustrated in FIG. 10B, moves the template data item C101 close to the affected area in order to measure the size by turning and moving the template data item C101. In the example illustrated in FIG. 10B, the user can confirm that the selected template data item C101 does not fit the affected area in size since the template data item C101 is larger than the affected area.

After confirming that the template data item C101 does not fit the affected area in size, the user re-selects a template data item smaller than the template data item C101 on the screen portion W102. In the example illustrated in FIG. 10C, template 3 is selected.

After template-data-item switching is performed by a user's operation, the template data switching unit 115 temporarily stores, in the position storing unit 116, position information of the criterion line CL101 and criterion point CP101 of the template data item C101 displayed before the switching.

After the template data switching unit 115 finishes storing the position information of the criterion line CL101 and criterion point CP101 of the template data item C101 in the position storing unit 116, the template data switching unit 115 reads a selected template data item C102 from the template data storing unit 111.

The template data switching unit 115 also refers to the position information, stored in the position storing unit 116, of the criterion line CL101 and criterion point CP101 of the template data item C101, as well as reading the selected template data item C102. Based on the position information the template data switching unit 115 refers to, the template data switching unit 115 displays the template data item C102 on the display unit 113 (the screen portion W103).

FIG. 10C illustrates a state after the template data switching unit 115 has performed the template-data-item switching. The displayed template data item C102 has the criterion line CL102 and the criterion point CP102. Referring to the criterion line and point stored in the position storing unit 116 of the template data item before it is switched, the template data switching unit 115 displays the switched template data item at a position having a different criterion point, with it turned by a turn angle of the criterion line.

Next, a template-data-item switching process of the template data switching unit 115 is described below with reference to FIG. 11.

Figure 11:
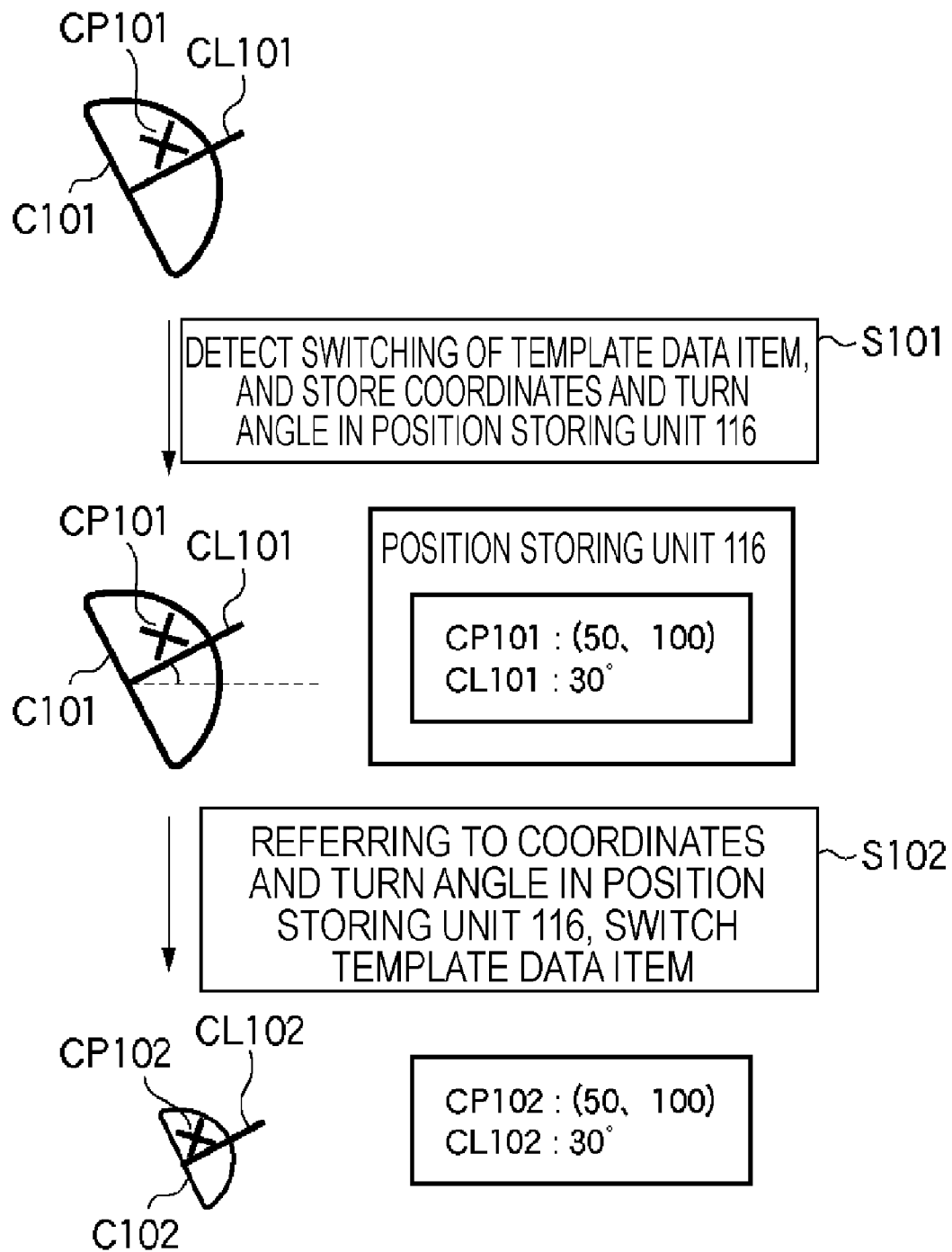
FIG. 11 is a flow diagram illustrating a template data switching process of a template data switching unit in the third embodiment.

FIG. 11 is a flow diagram illustrating the template-data-item switching process of the template data switching unit 115 in the present embodiment of the present invention.

When the template data switching unit 115 detects occurrence of the template-data-item switching, the template data switching unit 115 stores, in the position storing unit 116, coordinates of the criterion point CP101 corresponding to the template data item C101 in a state before the template data item C101 is switched, and a turn angle of the criterion line CL101 (step S101).

Next, the criterion point CP102 is displayed at a position identical to a position represented by the coordinates of the criterion point CP101, in which the criterion point of the template data item C102 obtained after the switching is stored in the position storing unit 116, and the criterion line CL102, which is turned by the turn angle of the criterion line CL101, is displayed (step S102).

The above process makes it possible to display the switched template data item at a position targeted by the user, even if the template-data-item switching occurs. Accordingly, the user can measure a template data item size without performing operations such as turning and moving. Thus, the user's working efficiency is improved.

While in the example illustrated in FIG. 11, template-data-item switching is executed using both a pair of coordinates of a criterion point and a turn angle of a criterion line, the template-data-item switching can be executed using only pair of coordinates.

As described above, according to the present embodiment, even if the user re-selects a template data item, the template data item can be displayed in overlay form at a targeted position. Therefore, the user can easily determine the size of an implant, resulting in a reduction in user operation time.

The display unit 113 displays the screen W101 for displaying a template data item on an X-ray image for implant size determination. The template-data-item switching method for a case in which only one template data item is displayed on the screen portion W103 has been described. Conversely, a template-data-item switching method for a case in which a plurality of template data items is displayed on the screen portion W103 is described below.

Figure 12A:
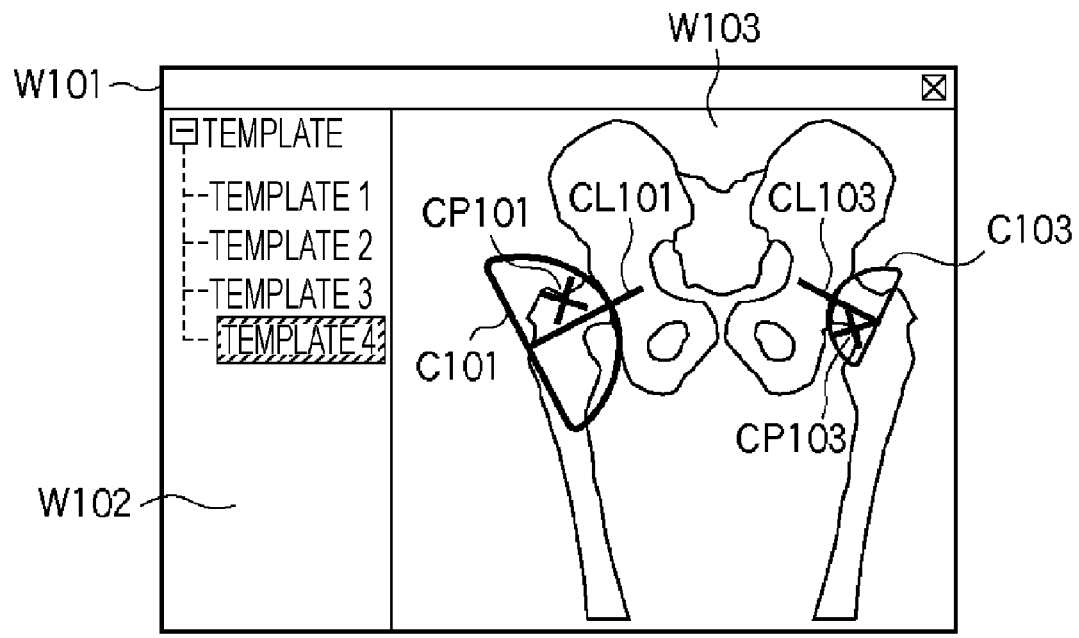
FIGS. 12A and 12B are illustrations of examples of displayed template data items.

The screen W103 illustrated in FIG. 12A displays two template data items C101 and C103. In order for the user to measure the size of the right leg joint, to the template data item C101 will need to be turned and moved. Since the template data item C101 is too large, the user will need to switch to a template data item smaller than the template data item C101.

Accordingly, the user switches the template data item C101 by selecting template 3 on the screen portion W102 by using the instruction input device. At this time, as described in the fourth embodiment, the template data switching unit 115 stores, in the position storing unit 116, coordinates of a criterion point and a turn angle of a criterion line for a template data item in a state before template-data-item switching.

However, in FIG. 12A, two template data items are displayed. Accordingly, when a plurality of template data items are displayed on the screen portion W103, the template data switching unit 115 stores, in the position storing unit 116, criterion-point coordinates and criterion-line turn angle of the template data item selected by the template data selecting unit 114.

Specifically, in the case in FIG. 12A, the template data item C101 is selected. Accordingly, when the instruction input device generates template-data-item switching, the template data switching unit 115 stores criterion-point coordinates and criterion-line turn angle of the template data item C101 in the position storing unit 116.

Figure 12B:
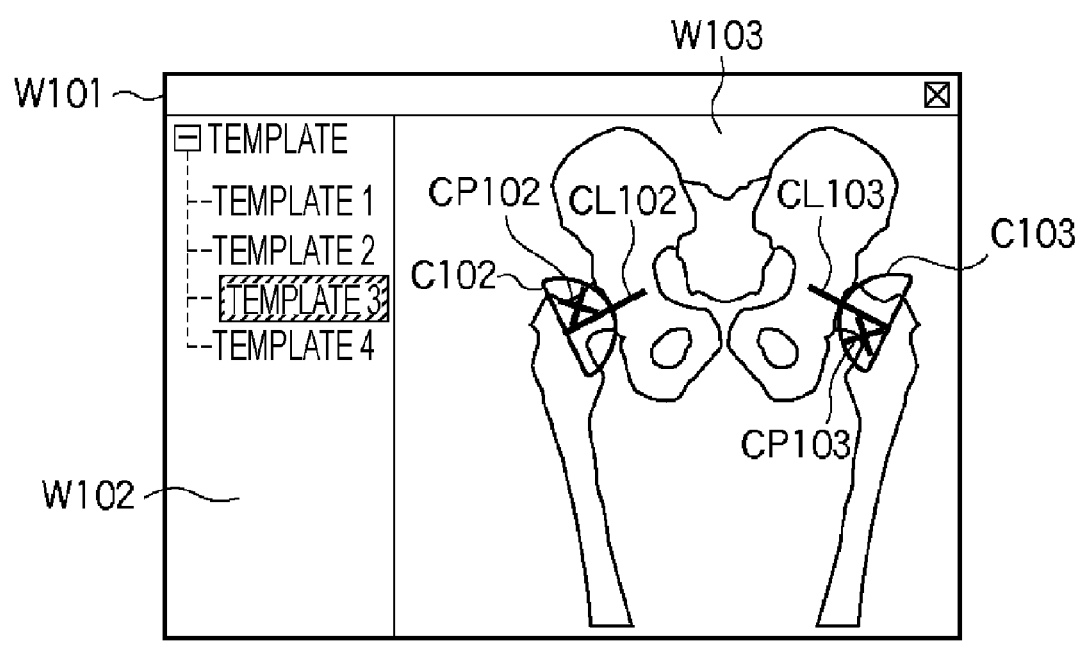

FIG. 12B illustrates a state after the template data switching unit 115 has performed the template-data-item switching.

The template data switching unit 115 stores the criterion-point coordinates and criterion-line turn angle of the template data item C101 in the position storing unit 116. Accordingly, the template data item C102, after the switching, is displayed by referring to the criterion-point coordinates and criterion-line turn angle stored in the position storing unit 116. Therefore, after the switching, the state illustrated in FIG. 12B appears. The user can display a template data item at a targeted position without turning and moving the template data item.

As described above, even if an operation is performed by using a plurality of template data items regarding a selected template data item to be operated, information of criterion line and criterion point of the template data item is stored in the position storing unit 116. This makes it possible that, even if the user switches a template data item (selected before the template data item is switched) to be operated, a template data item obtained after the switching is appropriately disposed.

Figure 13A:
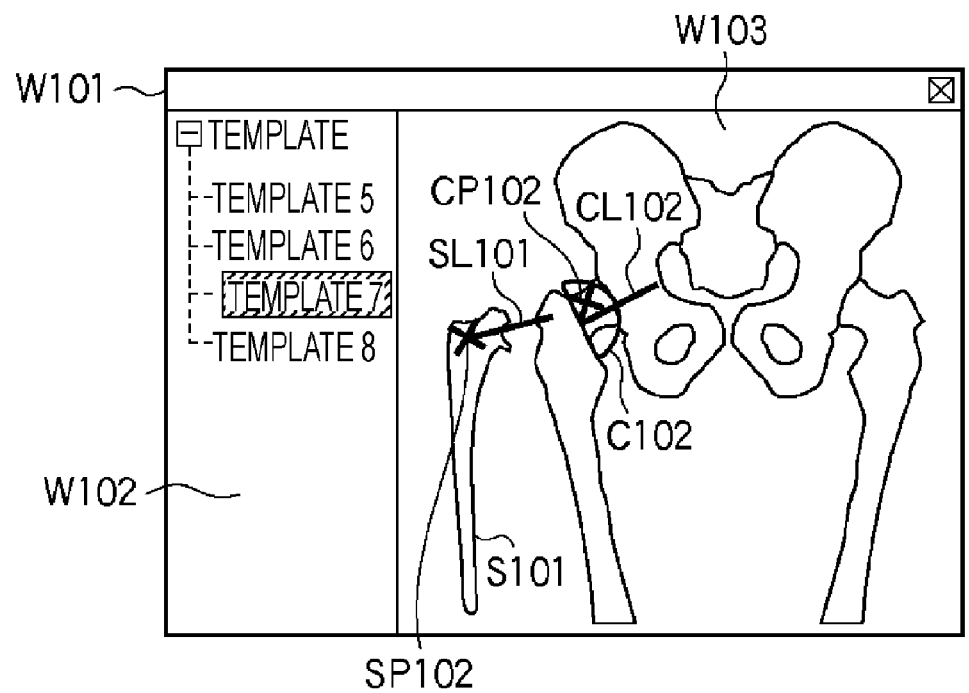
FIGS. 13A and 13B are illustrations of examples of displayed template data items.
Figure 13B:
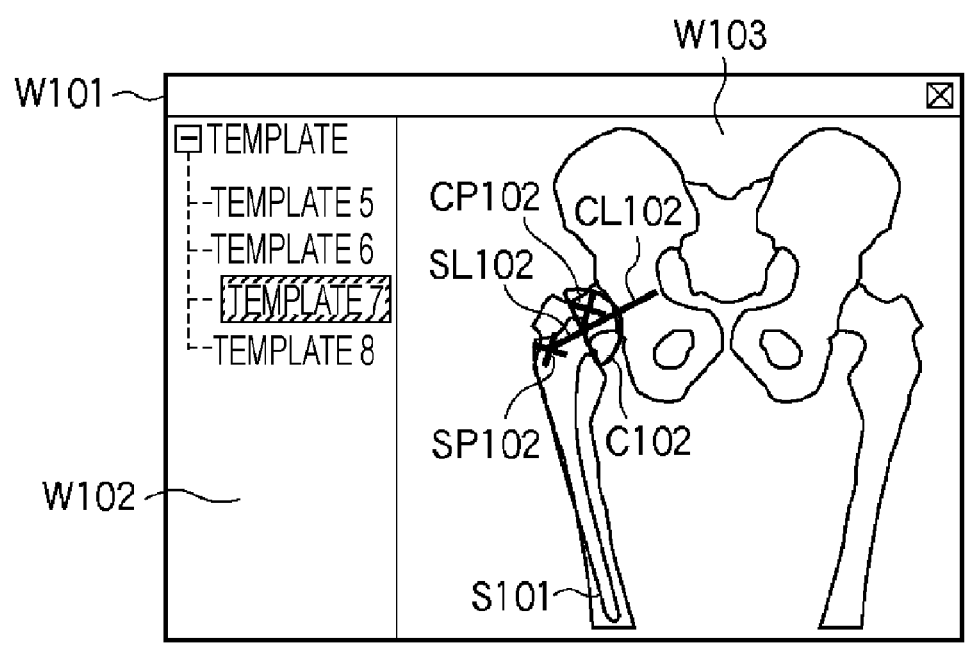

FIGS. 13A and 13B are illustrations of display examples of template data items in the fourth embodiment. In order for the user to determine an implant size, the display unit 113 displays a screen W101 on which template data items are shown on an X-ray image in overlay form for implant size determination. Here, an example of displaying template data items having different shapes on the screen portion W103 is shown.

In each of FIGS. 13A and 13B, there has already been a template data item C102 and the template data item C102 has a criterion line CL102.

By operating the instruction input device, the user displays, on the screen portion W103, a template data item S101 that is different in shape from the template data item C102. In other words, when template 7 is selected on the screen portion W102, the selected template data item is displayed on a screen portion W103.

The selected template data item S101 has a criterion line SL101. Normally, as illustrated in FIG. 13A, selection of a template data item different in shape displays a template data item S101 at an appropriate position on the screen portion W103.

In the fourth embodiment however, as illustrated in FIG. 13B, both template data items are displayed with the criterion line CL102 of the template data item C102 and the criterion line SL101 of the template data item S101 superposed on each other. In addition, both template data items may be displayed with the criterion point CP102 of the template data item C102 and the criterion point SP101 of the template data item S101 superposed on each other.

As described above, according to the fourth embodiment, in a case in which, for an already displayed template data item, a different template data item is additionally displayed, a display position of the different template data item is determined based on criterion points and lines of both data items. This makes it possible to display a template data item different in shape at a targeted position without turning the template data item.

Figure 14A:
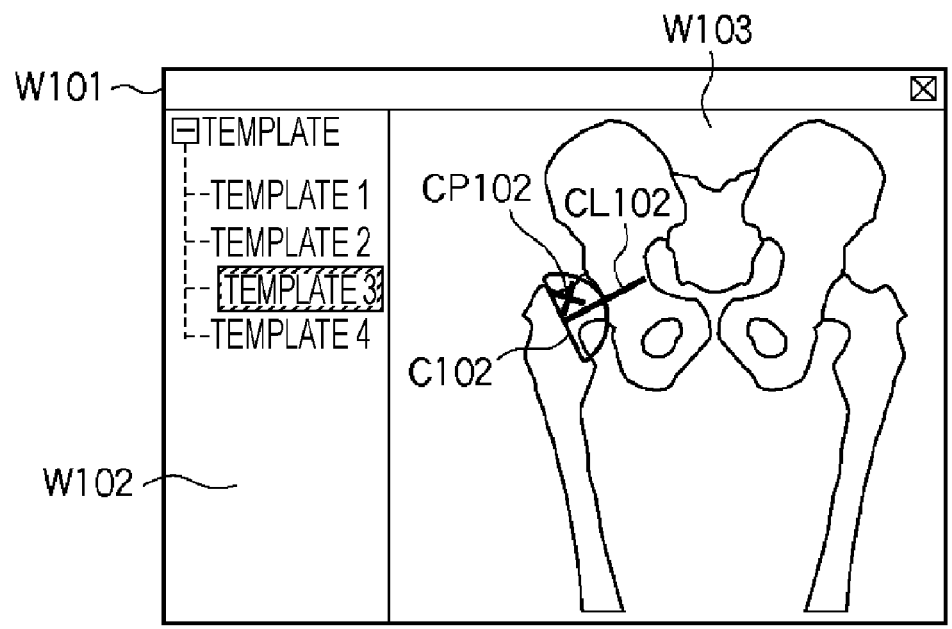
FIGS. 14A and 14B are illustrations of examples of displayed template data items.
Figure 14B:
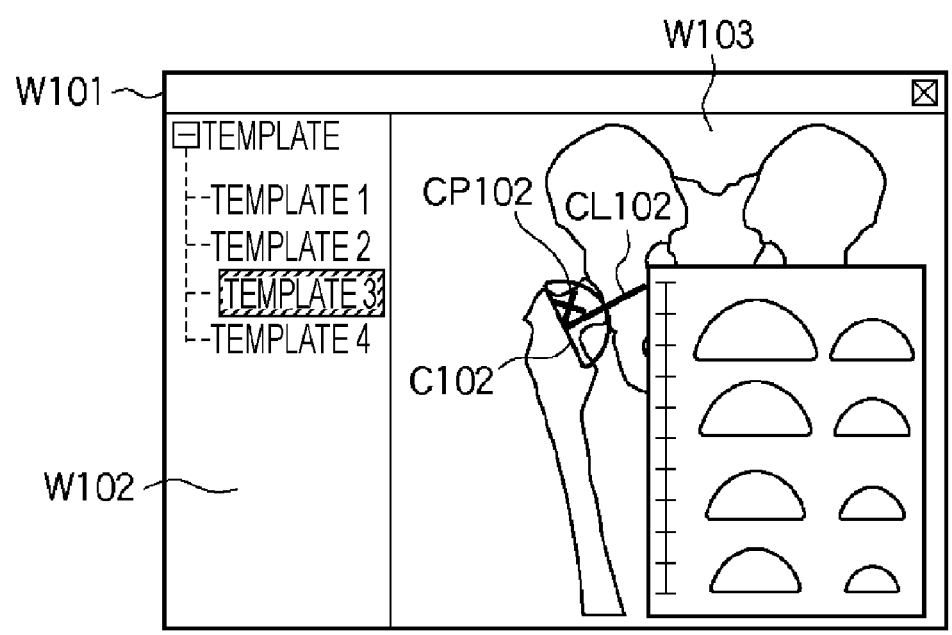

The template data processing device according to the present embodiment can display an image formed by imaging and an overlaid template data item in their actual sizes on the display unit 113 (or the display unit 22). In addition, in the template data processing device according to the present embodiment, for a segmented template data item (standard model data item), original data for template data items including a standard model date item prior to segmentation can be displayed. More specifically, when the instruction input device is used to issue an instruction to display original data of a template data item C102 in FIG. 14A, as illustrated in FIG. 14B, the original data is read from the template data storing unit 111 and is displayed on the display unit 113.

Original data of a template data item includes information such as a manufacturer of the template data item. Thus, by displaying the original data of the template data item on the display unit 113, the manufacturer of the implant can be easily confirmed, which is useful for such things as ordering an implant for actual use.

When a plurality of template data items are displayed on the display unit 113, each template data item can be displayed or hidden depending on the use or purpose of the template data item. In other words, by using the instruction input device to issue an instruction to hide a template data item selected by the template data selecting unit 114, the display unit 113 can temporarily hide the template data item. This makes it possible that, if too many template data items are displayed on the display unit 113, a targeted template data item can be temporarily displayed.

The template data processing device according to the present embodiment includes the measurement unit 117 of the data processing device shown in FIG. 8. By referring to measurement values obtained by the measurement unit 117, and reading a template data item having an optimal size from the template data storing unit 111, the read template data item can be displayed on the display unit 113.

More specifically, presuming that a circle passing through three points (a criterion point and ends of a criterion line) is drawn by the measurement unit 117, with its diameter set to 50 centimeters, a template data item corresponding to the diameter of 50 centimeters is read from the template data storing unit 111, and is displayed on the display unit 113. In other words, a template data item is selected and displayed on the display unit 113. This can efficiently execute a template data item selecting operation.

In each of the foregoing embodiments, artificial bone implant templates are described as examples of templates. However, the templates are not limited to the artificial bone implant templates. For example, the present invention is applicable to data processing based on medical images and using templates concerning various types of implants such as artificial skin, tooth profile, artificial teeth, artificial vessels, artificial valves, grafts, transplantation tissue, etc.

The template sheets have been described using an example of a case in which q template sheet is created considering an enlargement factor of an X-ray image. However, an X-ray image can be reduced depending on an apparatus configuration. In this case, a template created considering a reduction in X-ray image is used.

The present invention is applicable to a system including a plurality of apparatuses, as well as to an apparatus formed by a single unit. The present invention can be implemented by supplying a storage medium on which program codes of software for realizing the functions of the above described embodiments are recorded to a system or apparatus and by causing a computer (CPU or MPU) pf the system or apparatus to read and execute the program codes stored on the storage medium.

In this case, the program codes themselves read from the storage medium realize the functions of the above described embodiments. Thus, the storage medium that stores the program codes constitutes the present invention.

The storage medium for supplying the program include, for example, a floppy disk a hard disk, an optical disk, a magnetic-optical disc, a CD-ROM, a CD-R, a CD-RW, a magnetic tape, a nonvolatile memory card, a ROM, a DVD, etc.

In addition, as a program supplying method, a browser of a client computer is used to access a site on the Internet. The program can be supplied by downloading from the accessed site, to a recording medium such as a hard disk, the computer program in the embodiment, or a compressed file having an automatic installation function.

Furthermore, the program supplying method can be realized by dividing the program code of the program in the embodiment into a plurality of files and downloading the files from different sites. That is, a WWW (World Wide Web) server that allows downloading by a plurality of users of program files for realizing the functions of the embodiment is included in the present invention.

Moreover, the program of the embodiment is distributed to users, with the program stored in encrypted form in storage media such as CD-ROMs, and a user that satisfies predetermined conditions is allowed to download key information from a site via the Internet. By using the key information to execute and install the encrypted program into the computer, the program can be executed.

In addition, the above-described functions of the embodiment are realized such that the computer executes the read program. On the basis of instructions of the program, an operating system running on the computer performs all or part of actual processing, and the processing can realize the above-described functions.

The program that is read from a recording medium is written into a function expansion board built into the computer and a memory provided in a function expansion unit connected to the computer. After that, a CPU included in the function expansion board or function expansion unit performs all or part of actual processing, and the processing realizes the above-described functions of the embodiment.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-019768 filed Jan. 27, 2006, which is hereby incorporated by reference herein in its entirety.

What is claimed is:

1. An information processing apparatus for displaying, on a medical image, template data corresponding to an implant, the information processing apparatus comprising:
   a storage unit configured to store the template data and a predetermined portion distance of a predetermined portion of a representation by the template data;
   a display unit configured to display the template data stored in the storage unit;
   a measurement unit configured to measure length information of the template data displayed on the display unit;
   a specification unit configured to specify an error range of variable magnification of the template data displayed on the display unit; and
   a judgment unit configured to determine, based on the length information measured by the measurement unit and the predetermined portion distance stored by the storage unit, whether the variable magnification of the template data displayed on the display unit is within the error range specified by the specification unit.

2. The information processing apparatus according to claim 1, wherein the storage unit stores variably magnified distance data based on considering a variable magnification of the template data for the medical image, and wherein, based on the predetermined portion distance and variably magnified distance data stored in the storage unit, the judgment unit determines whether the variable magnification of the displayed template data is within the error range specified by the specification unit.

3. The information processing apparatus according to claim 1, further comprising an input unit configured to input, as data, one or both of the predetermined portion distance and the variable magnification of the template data for the medical image,
   wherein, based on the data input by the input unit, the judgment unit determines whether the variable magnification of the template data displayed on the display unit is within the error range specified by the specification unit.

4. The information processing apparatus according to claim 1, further comprising a correction configured to correct a resolution of the template data based on the determination by the judgment unit,
   wherein, when the judgment unit determines that the variable magnification of the displayed template data is not within the error range specified by the specification unit, the correction unit corrects the resolution of the template data.

5. The information processing apparatus according to claim 4, wherein, when the correction unit corrects the resolution of the template data, the measurement unit re-measures the length information, and, when variable magnification obtained from the length information measured by the re-measure is within the error range specified by the specification unit, the template data having the corrected resolution is stored in the storage unit.

6. The information processing apparatus according to claim 1, further comprising:

a segmentation unit configured to segment specified standard model data as the template data from a group of template data including a plurality of types of standard model data displayed on the display unit; and a control unit configured to permit or prohibit a segmentation operation by the segmentation unit based on a determination result of the judgment unit, wherein, when the judgment unit determines that the variable magnification of the displayed template data is within the error range specified by the specification unit, the control unit permits the segmentation operation by the segmentation unit.

7. A method for displaying, on a medical image, template data corresponding to an implant, the method comprising:

using a processor to perform steps comprising:

storing the template data and a predetermined portion distance of a predetermined portion of a representation by the template data;

displaying the stored template data;

measuring length information of the displayed template data;

specifying an error range of the variable magnification of the displayed template data; and determining, based on the measured length information and the stored predetermined portion distance, whether the variable magnification of the displayed template data is within the specified error range.

8. A computer-readable non-transitory storage medium storing computer-executable process steps for causing a computer to execute the method of claim 7.

* * * * *